United States Patent [19]
Olson et al.

[11] Patent Number: 5,906,619
[45] Date of Patent: May 25, 1999

[54] DISPOSABLE DELIVERY DEVICE FOR ENDOLUMINAL PROSTHESES

[75] Inventors: Steve L. Olson, Cupertino; Glenn R. Davis, Sunnyvale, both of Calif.

[73] Assignee: Medtronic, Inc., Minneapolis, Minn.

[21] Appl. No.: 08/898,997

[22] Filed: Jul. 24, 1997

[51] Int. Cl.$^6$ .................................................. A61F 11/00
[52] U.S. Cl. ..................... 606/108; 606/191; 606/194; 606/195
[58] Field of Search ................................. 606/108, 191, 606/194, 195; 623/1, 11, 12

[56] References Cited

U.S. PATENT DOCUMENTS

| 5,433,723 | 7/1995 | Lindenberg et al. | 606/198 |
| 5,683,451 | 11/1997 | Lenker et al. | 623/1 |
| 5,749,921 | 5/1998 | Lenker et al. | 623/1 |
| 5,755,773 | 5/1998 | Evans et al. | 623/1 |

FOREIGN PATENT DOCUMENTS

| 0 274 846 A1 | 7/1988 | European Pat. Off. | A61M 29/02 |
| 0 361 314 A2 | 4/1990 | European Pat. Off. | A61M 25/01 |
| 0 732 087 A1 | 3/1995 | European Pat. Off. | A61F 2/06 |
| WO 93/15790 | 8/1993 | WIPO | A61N 1/00 |

*Primary Examiner*—Michael Buiz
*Assistant Examiner*—Vy Quang Bui
*Attorney, Agent, or Firm*—Townsend and Townsend and Crew LLP

[57] ABSTRACT

Improved systems, devices, and methods for deployment of endoluminal prostheses within the lumens of the body withdraw a sheath from over the tightly compressed prostheses using an actuation mechanism having a variable mechanical advantage. This allows movement of the sheath to be initiated with ease and accuracy. Once deployment is safely underway, and after static frictional forces have been overcome, the remainder of the deployment may proceed more rapidly without significantly degrading overall safety or ease of use of the delivery system. In another improvement, the handle for the actuation mechanism may rotate about an axis parallel to the axis of the sheath. An outer tube may be provided around the sheath and coupled to the prosthesis restraining member within the sheath. The outer tube may be inserted through an introducer valve, so that friction between the outer tube and introducer valve helps restrain the prosthesis as the sheath is withdrawn proximally relative to both the member and the outer tube.

24 Claims, 12 Drawing Sheets

DISPOSABLE DELIVERY DEVICE FOR ENDOLUMINAL PROSTHESES

BACKGROUND OF THE INVENTION

1. Field of the Invention

The present invention generally relates to tubular endoluminal prostheses, such as stents, stent-grafts, and the like. More particularly, the present invention provides improved delivery systems and methods for their use to accurately and safely deploy endoluminal prostheses within the lumens of the body, particularly within the vascular system for treatment of aortic aneurysms, stenoses, and the like.

Vascular aneurysms are the result of abnormal dilation of a blood vessel, usually resulting from disease and/or genetic predisposition, which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending into one or both of the iliac arteries.

Aortic aneurysms are now commonly treated in open surgical procedures where the diseased vessel segment is bypassed and repaired with an artificial vascular graft. While considered to be an effective surgical technique, particularly considering the alternative of a usual fatal ruptured abdominal aortic aneurysm, conventional vascular graft surgery suffers from a number of disadvantages. The surgical procedure is complex and requires experienced surgeons and well-equipped surgical facilities. Even with the best surgeons and equipment, however, patients being treated frequently are elderly and weakened from cardiovascular and other diseases, reducing the number of eligible patients. Even for eligible patients prior to rupture, conventional aneurysm repair has a relatively high mortality rate, usually from 2% to 10%. Morbidity related to the conventional surgery includes myocardial infarction, renal failure, impotence, paralysis, and other conditions. Additionally, even with successful surgery, recovery takes several weeks, and often requires a lengthy hospital stay.

In order to overcome some or all of these drawbacks, endovascular prosthesis placement for the treatment of aneurysms has been proposed. Although very promising, many of the proposed methods and apparatus suffer from undesirable limitations. In particular, accurate delivery and placement of the endovascular prosthesis within the vasculature can be problematic.

Stent-grafts are often resilient structures, biased to expand against the surrounding lumenal wall. Such resiliently-expanding stent-grafts are tightly compressed within the catheter, imposing significant forces against the surrounding catheter sheath. This can often lead to excess friction between the stent-graft and the sheath, particularly when the resiliently-expanding structure invaginates into the catheter material. As these catheters are often required to maneuver within the tortuous vascular system, catheter sheaths are often formed as flexible, elongate bodies which are particularly susceptible to vagination of the tightly compressed stent-graft in the flexible material of the catheter wall.

For these reasons, it would be desirable to provide improved devices, systems, and methods for endoluminal deployment of prostheses such as stents, stent-grafts, and the like, for treatment of aneurysms and other diseases of the body lumens. It would be particularly desirable if such improved systems and methods enhanced the accuracy and safety of the deployment procedure, without significantly increasing deployment time, equipment costs, or complexity of the deployment procedure.

2. Description of the Background Art

Devices for endoluminal placement of prostheses are described in U.S. Pat. Nos. 4,512,338, 4,651,738, 4,665,918, 5,458,615, 5,480,423, 5,484,418, 5,489,295, 4,990,151, 5,035,706, 5,433,723, 5,443,477, 5,282,824, 5,275,622, 5,242,399, 5,201,757, 5,190,058, 5,104,399, 5,092,877, 4,990,151, and EP Patent Publication Nos. EP 0 539 237 A1, 0 518 839 A2, EP 0 505 686 A1, and EP 0 508 473 A2.

SUMMARY OF THE INVENTION

The present invention provides improved systems, devices, and methods for deployment of endoluminal prostheses within the lumens of the body, and particularly for deployment of stents and stent-grafts within the vascular system. In a first improvement over known delivery systems, a sheath is withdrawn from over a tightly compressed prostheses using an actuation mechanism having a variable mechanical advantage, which varies with the position of the sheath. This allows movement of the sheath to be initiated with ease and accuracy. Once deployment is safely underway, and after static frictional forces have been overcome, the remainder of the deployment may proceed more rapidly, without significantly degrading overall safety or ease of use. In another improvement, the handle for the actuation mechanism may rotate about an axis parallel to the axis of the sheath, thereby avoiding any inadvertent proximal and distal movement imparted by the handle to the prosthesis or delivery system. Accuracy and ease of use of the delivery system may also be improved by providing an outer tube around the sheath which is coupled to the prosthesis restraining member within the sheath. The outer tube may be inserted through an introducer valve, so that friction between the outer tube and introducer valve helps restrain the prosthesis at the target position as the sheath is withdrawn proximally.

In a first aspect, the present invention provides a delivery system for use with a tubular endoluminal prosthesis. The delivery system comprises a sheath having a proximal end, and a distal end, and a lumen. The lumen is capable of receiving the prosthesis near the distal end. The member in the lumen of the sheath is adapted for expelling the prosthesis from the lumen as the sheath moves from a first position to a second position relative to the member. An actuation mechanism is attached to the member, and couples a handle to the sheath with a mechanical advantage that varies as the sheath moves between the first position and the second position.

Generally, a displacement of the handle effects a first displacement of the sheath relative to the member when the sheath is adjacent the first position. This same handle displacement effects a significantly greater displacement of the sheath relative to the member when the sheath is adjacent to the second position. Typically, the initial mechanical advantage is larger to overcome static frictional forces between the prosthesis and the sheath, allowing the sheath to be withdrawn slowly and precisely. Once the sheath has begun sliding over the prosthesis, and in some embodiments, once an end of the prosthesis has expanded to engage the surrounding luminal wall, the deployment may proceed at a more rapid rate by using a lower mechanical advantage.

In another aspect, the present invention provides a prosthetic delivery system for use with a radially expandable tubular endoluminal prosthesis. The delivery system comprises a sheath having a proximal end, a distal end, an axis therebetween, and a lumen capable of receiving the prosthesis near the distal end. A member is disposed in the lumen for expelling the prosthesis from the lumen as the sheath moves from a first position to a second position relative to the member. An actuation mechanism is attached to the member, and couples the sheath to a handle. The handle is rotatable about an axis substantially parallel to the axis of the sheath to effect movement of the sheath from the first position to the second position.

In another aspect, the invention provides a delivery system for inserting a tubular endoluminal prosthesis into a patient body. The delivery system comprises a sheath having a proximal end, a distal end, and a lumen capable of receiving the prosthesis near the distal end. A member is disposed in the lumen, and is adapted for expelling the prosthesis from the lumen as the sheath moves from a first position to a second position relative to the member. An outer tube is disposed over the sheath. A housing is attached to the member near the proximal end of the sheath, and is coupled to the outer tube so that the outer tube remains substantially axially aligned with the member when the sheath moves from the first position to the second position. The outer tube will often be insertable into an introducer valve, so that friction between the outer tube and the introducer valve will help hold the prosthesis at the target location during deployment.

In a method according to the present invention, a radially expandable tubular endoluminal prosthesis is positioned at a target location in a body lumen within a lumen of a sheath. The prosthesis is released from the sheath by actuating a handle. This withdraws the sheath proximally from a first position to a second position. A displacement of the handle effects a first displacement of the sheath when the sheath is adjacent to the first position. The same handle displacement effects a second displacement of the sheath which is different than the first sheath displacement when the sheath is adjacent to the second position.

In another method provided by the present invention, a radially expandable tubular endoluminal prosthesis is deployed by positioning the prosthesis at a target location in a body lumen while the prosthesis is disposed within a lumen of a sheath. The prosthesis is released from the sheath by rotating a handle. The handle rotates about an axis which is parallel to an axis of the sheath, and moves the sheath axially from over the prosthesis.

In yet another method of the present invention, a radially expandable tubular endoluminal prosthesis is deployed by inserting the prosthesis into the body lumen through an introducer valve. The prosthesis is inserted while disposed within a lumen of a sheath. An outer tube is also inserted through an introducer valve, and the prosthesis is positioned at a target location in the body lumen. The prosthesis is released from the sheath by withdrawing the sheath and restraining the prosthesis with a member disposed in the sheath. This member is axially restrained relative to the outer tube while releasing the prosthesis, so that friction between the introducer valve and the outer tube helps prevent movement of the prosthesis from the target location.

DESCRIPTION OF THE PREFERRED EMBODIMENT

The present invention provides delivery devices, systems, and methods for delivering radially expandable tubular prostheses, particularly stents, stent-grafts, and the like. The delivery structures and methods of the present invention are suitable for a wide variety of therapeutic uses, including stenting of the ureter, urethra, trachea, branchi, esophagus, biliary tract, and the like. The structures and methods will also be useful for creating temporary or long-term lumens, such as for the formation of fistulas. The present invention will find its most immediate application for delivery of endovascular prostheses as a treatment for diseases of the vasculature, particularly for treating aneurysms, stenoses, and the like.

The structures and methods described hereinbelow will find use in deployment of axially uniform cylindrical prostheses, of pre-assembled bifurcated prostheses, and of prosthetic modules for selective assembly, either prior to deployment or in situ. Modular prosthetic structures and delivery methods are more fully described in co-pending U.S. patent application Ser. Nos. 08/704,960, filed Aug. 29, 1996 (Attorney Docket No. 16380-003410); 08/538,706, filed Oct. 3, 1995 (Attorney Docket No. 16380-003800); and 60/028,928, filed Oct. 7, 1996 (Attorney Docket No. 16380-004110), the full disclosures of which are incorporated herein by reference.

Figure 1:
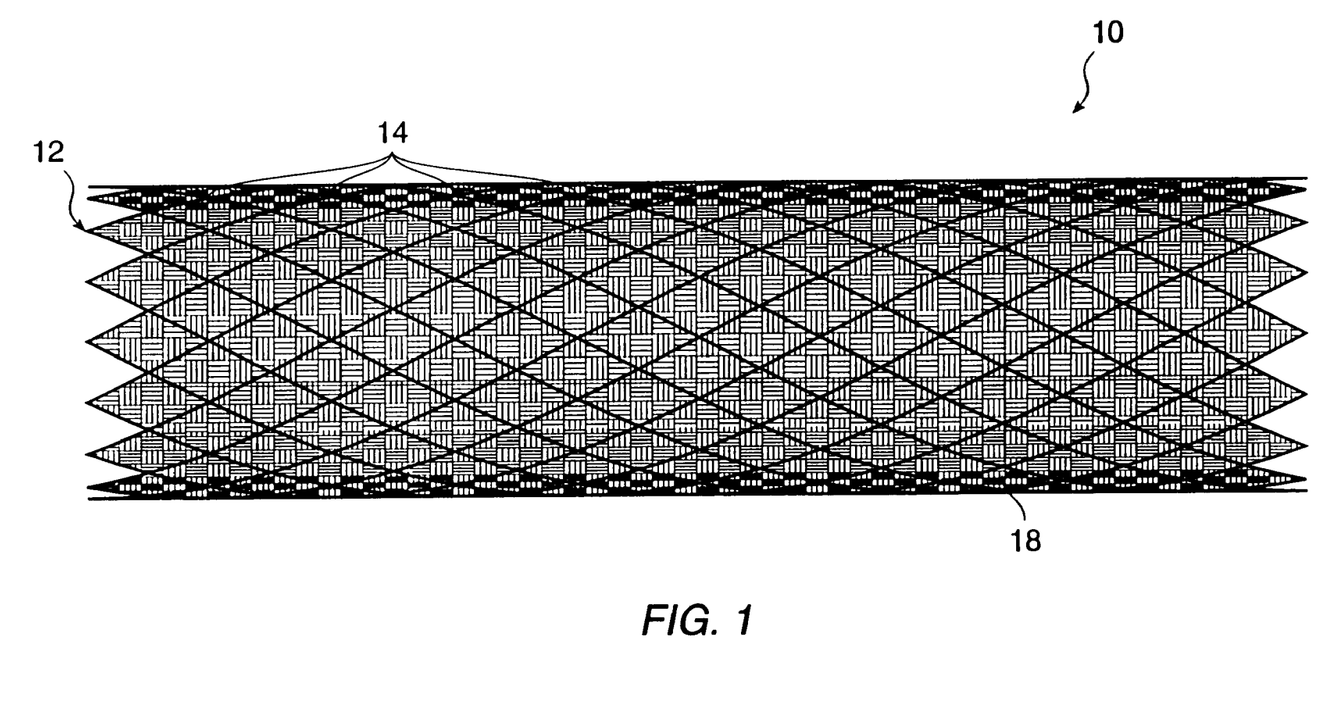
FIG. 1 is a simplified side view of an exemplary cylindrical vascular stent-graft.

Referring now to FIG. 1, an exemplary cylindrical prosthesis 10 comprises a preferred tubular frame 12 formed as a plurality of independent ring frames 14. Tubular frame 12 supports an inner liner 18. Optionally, an outer liner is disposed over the ring frames, either inside of inner liner 18, or in combination therewith.

To secure ring frames 14 to liner 18, the liner is typically sutured to the frame. A wide variety of alternative liner/frame attachment mechanisms are available, including adhesive bonding, heat welding, ultrasonic welding, and the like. Preferably, liner 18 is sutured along the extreme proximal and distal ends of frame 12 to enhance sealing between the liner and the surrounding body lumen.

Prosthesis 10 will typically have a length in the range from about 20 mm to 500 mm, preferably being 50 mm to 200 mm. A relaxed diameter of prosthesis 10 will generally be in the range from about 4 mm to 45 mm, preferably being in the range from about 5 mm to 38 mm.

Figure 2:
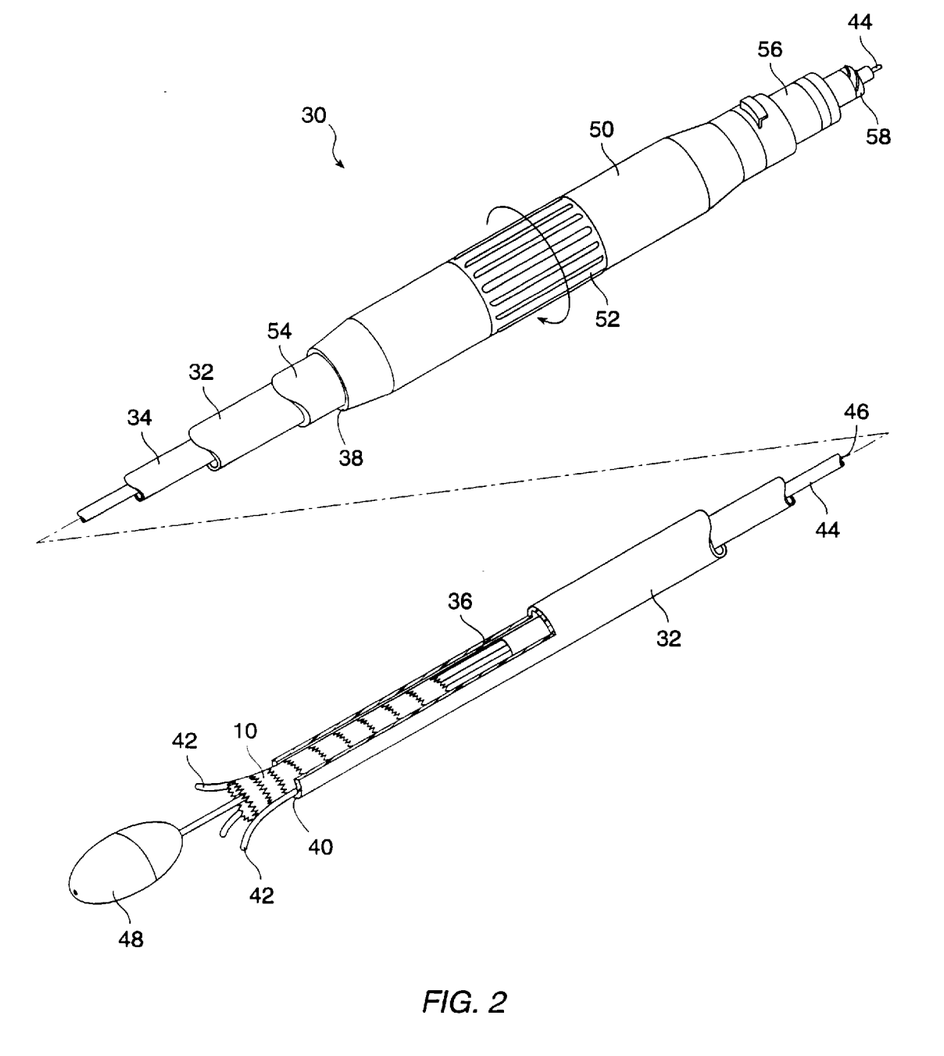
FIG. 2 is a perspective view of a delivery system according to the principles of the present invention.

Referring now to FIG. 2, an exemplary delivery system 30 comprises a tubular sheath 32 and a shaft 34. Sheath 32 has a lumen 36 extending from a proximal end 38 to a distal end 40. Shaft 34 is slidably received within lumen 36, and a plurality of runners 42 extend distally from the shaft. Runners 42 line a portion of the inner surface of lumen 36, and slide within the lumen of the shaft. Shaft 34 also has a lumen, in which a core shaft 44 is affixed. Core shaft 44 has a guidewire lumen 46. Nosecone 48 is affixed to the distal end of core shaft 44, and can therefore be manipulated with the runners. Alternatively, core shaft 44 may be slidably disposed within shaft 34 to allow independent manipulation of nosecone 48.

Prosthesis 10 is radially compressed and restrained within runners 42. In turn, sheath 32 prevents runners 42 from expanding outwardly. Runners 42 are preferably formed from a hard material, and distribute the expansive load from the frame of prosthesis 10 over the inner surface of lumen 36. Exemplary methods and devices for deploying prostheses using runners 42 are more fully described in U.S. patent application Ser. No. 08/475,200, filed Jun. 7, 1995 (Attorney Docket No. 16380-001130), the full disclosure of which is incorporated herein by reference.

A housing 50 is disposed at proximal end 38 of sheath 32. Housing 50 contains an actuation mechanism for withdrawing sheath 32 proximally while prosthesis 10 is axially restrained by runners 42 and shaft 34. To withdraw sheath 32 proximally, a handle 52 is rotated about the axis of the sheath, as illustrated. This avoids inadvertently imparting any axial movement of the delivery system from rotation of the handle during deployment, preventing prosthesis 10 from being displaced axially from the target location, and also avoiding any injury of the surrounding body lumen by inadvertently advancing runners 42.

An outer tube 54 extends distally from housing 50 over sheath 32. Shaft 34 extends through housing 50 and is affixed to a connector 56, which is releasably attached to the proximal end of housing 50. Thus, shaft 34 and outer tube 54 are coupled together through the housing, so that sheath 32 retracts proximally between these two structures when handle 52 rotates. Once the prosthesis is deployed and runners 42 slide proximally from between the prosthesis and surrounding body lumen, connector 56 may be uncoupled from housing 50 to draw runners 42 and the proximal portion of nose-cone 48 back into the distal end of sheath 32.

A luer fitting 58 is affixed to the proximal end of connector 56 to facilitate introducing a guidewire into guidewire lumen 46 of core shaft 44, or to allow the guidewire lumen to be sealed when not in use.

Figure 3:
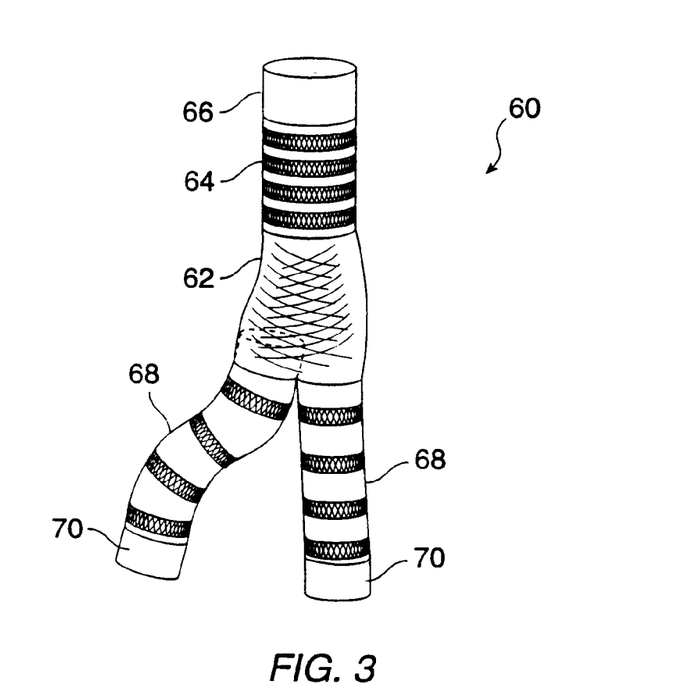
FIG. 3 illustrates an exemplary modular endoluminal bifurcated prosthesis.

Referring now to FIG. 3, an assembled branching endovascular prosthesis 60 comprises a relatively rigid lumen separation portion 62 between a trunk portion 64 and two branch portions 68. Lumen separation portion 62 may include a contiguous frame to provide relatively high column and hoop strength, while the branch end trunk portions may be formed with independent ring frames or a helical frame in which the loops are separated to enhance axial flexibility. Sealing cuffs 66 and 70 securely anchor the prosthesis against healthy tissue, and also seal the prosthetic lumen against the surrounding endolithium of the blood vessel.

Figure 4:
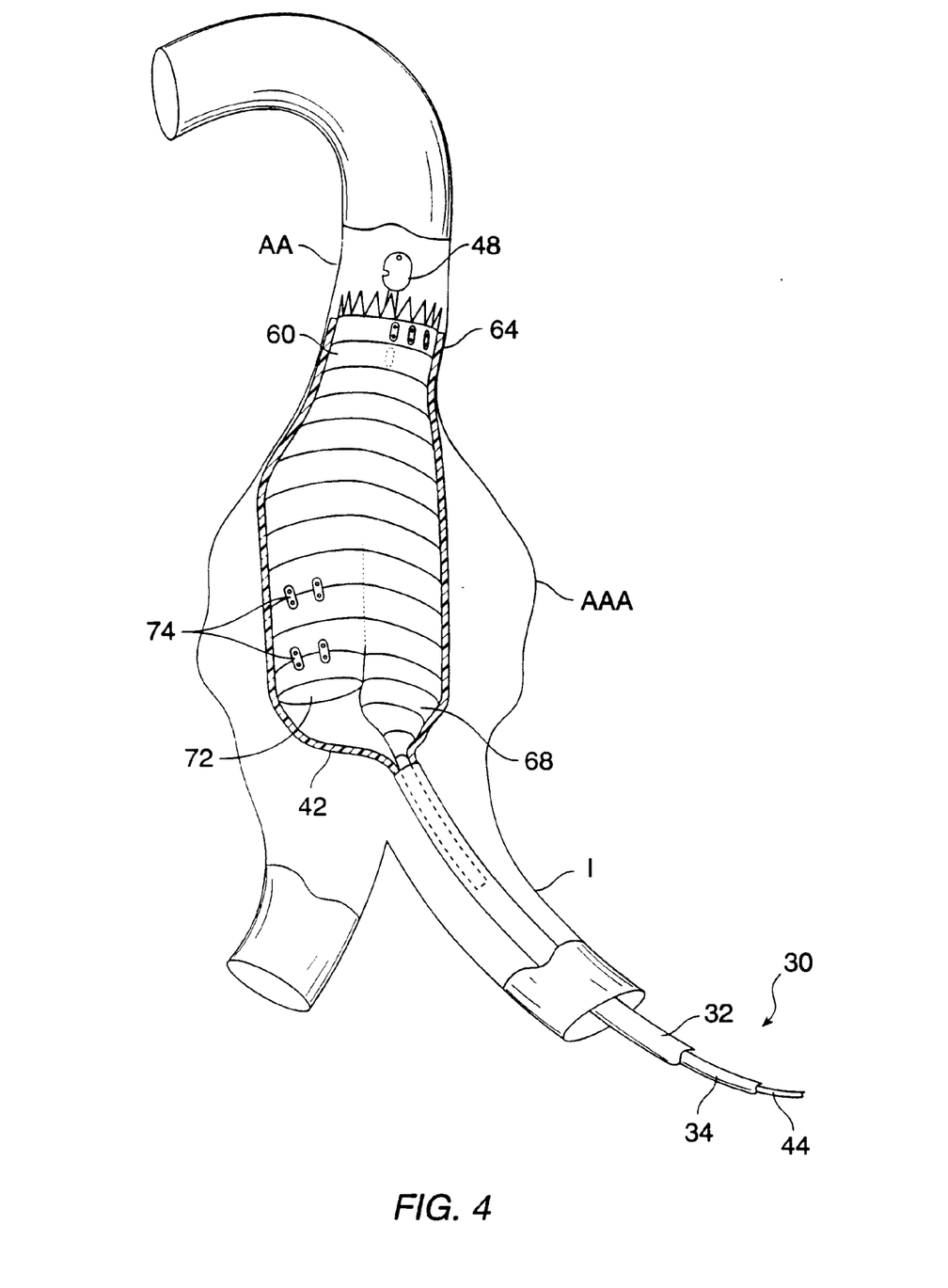
FIG. 4 illustrates a method for using the delivery system of FIG. 2 for deploying a bifurcated prosthetic module.

As schematically illustrated in FIG. 4, a bifurcated prosthetic module of bifurcated prosthesis 60 may be deployed using delivery system 30 to isolate an abdominal aortic aneurysm AAA. This initial prosthetic module extends from the abdominal aorta AA to a first iliac I, and has an open port 72 for receiving a cylindrical prosthetic module to effectively seal the distended aneurysm from the blood flow. The prosthetic module is deployed by axially restraining the module within runners 42 and withdrawing sheath 32 proximally. The runners, which typically comprise thin strips of a high-strength metal such as stainless steel, slide along the inner lumen of sheath 32 and flex outwardly as the prosthesis expends resiliently. Once the prosthetic module is fully expanded, the runners can be withdrawn proximally from between the prosthesis and the surrounding luminal wall, while the expanded prosthesis engages the luminal wall between the runners.

The bifurcated prosthetic module illustrated in FIG. 4 includes a pattern of discreet radiopaque markers 74 to facilitate positioning and assembly of the prosthetic modules fluoroscopically. The use and structure such radio-opaque markers is more fully described in U.S. patent application Ser. Nos. 08/628,797, filed Apr. 5, 1996 (Attorney Docket No. 16380-005600) and 08/877,151, filed Jun. 17, 1997 (Attorney Docket No. 16380-005710), the full disclosures of which are incorporated herein by reference.

Figure 5:
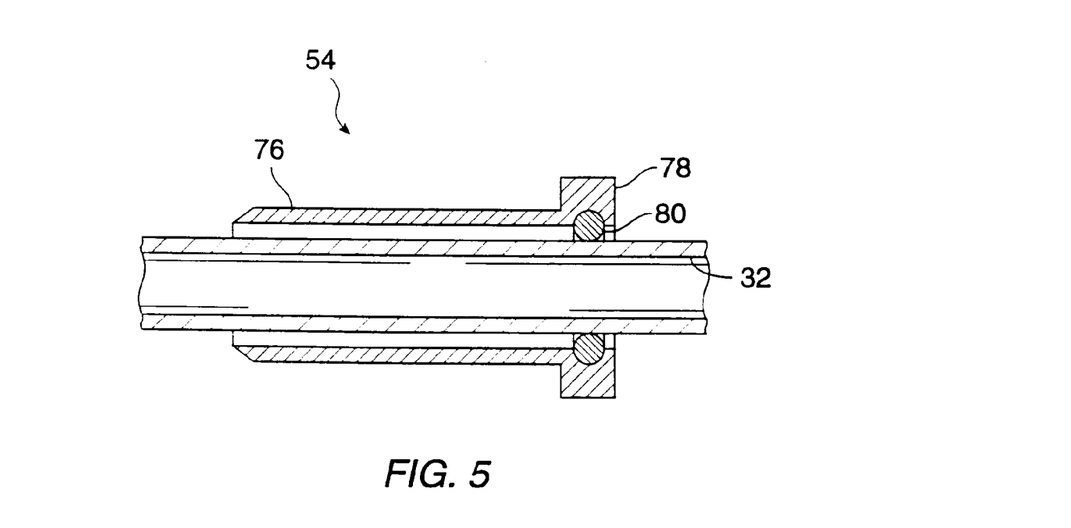
FIG. 5 illustrates an outer tube for use in the delivery system of FIG. 2 to provide a low-friction seal between an introducer valve and the delivery sheath.

Referring now to FIG. 5, outer tube 54 generally comprises a tubular body 76 and an endcap 78. An o-ring 80 is disposed within endcap 78, and provides a low friction hemostasis seal around the outer surface of sheath 32. As described above, the runners of the present invention facilitate smoothly retracting sheath 32 relative to the radially compressed prosthesis. However, a substantial amount of friction may be encountered between the outer surface of delivery system 30 and introducer sheath 82 at which the delivery system enters a patient's body 84.

Figure 6:
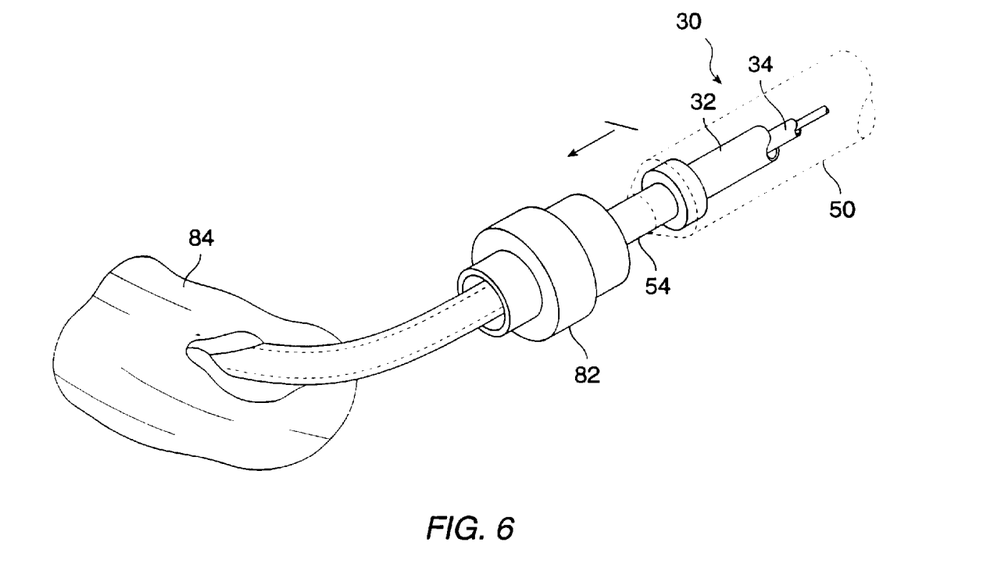
FIG. 6 illustrates a method for using the outer tube between the delivery sheath and an introducer valve to prevent movement of the prosthesis during deployment.

Introducer sheaths generally provide hemostasis around catheters, guidewires, other invasive surgical implements of various sizes and configurations. Such introducer sheaths typically include a resilient sealing body which radially engages the outermost layer of the delivery system. As it is generally desirably to leave the internal prosthesis at a fixed position while withdrawing sheath 32 proximally, such friction between introducer valve 82 and sheath 32 is generally disadvantageous. However, by coupling outer tube 54 to housing 50, as illustrated in FIG. 6, and by providing an actuation mechanism which withdraws sheath 32 relative to shaft 34 and housing 50, friction between outer tube 54 and introducer valve 82 may be used to help restrain the prosthesis at the target location during deployment.

To facilitate insertion of outer tube 54 into introducer valve 82, a distal end of tubular body 76 may be tapered. In some embodiments, introducer valve 82 may be actuated once outer tube 54 and the prosthesis are positioned, compressing the sealing body against the outer tube to lock the prosthesis in place. A particularly advantageous actuatable introducer valve is described in co-pending U.S. patent application Ser. No. 08/744,659, filed Nov. 6, 1996 (Attorney Docket No. 16380-006300), the full disclosure of which is incorporated herein by reference.

Figure 7:
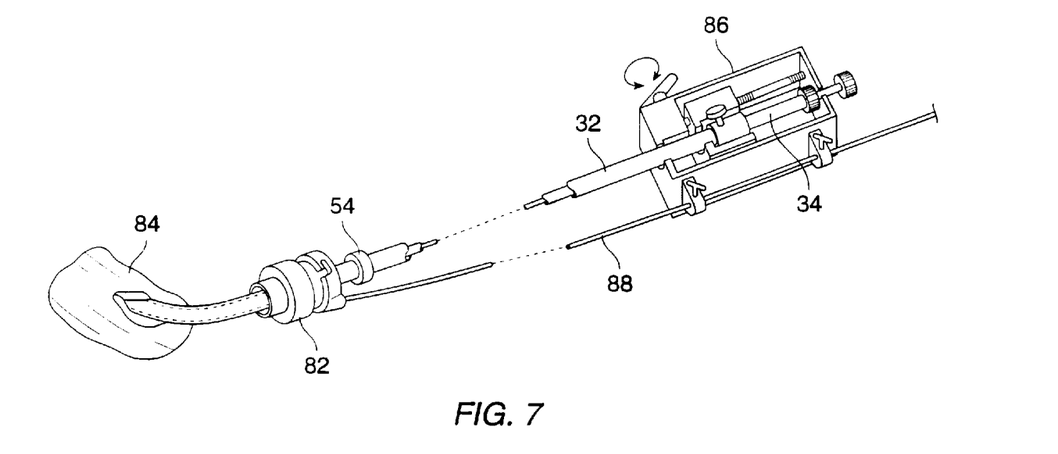
FIG. 7 illustrates an alternative delivery system which prevents relative motion between the introducer valve and the prosthesis with an external support rod.

An alternative system and method for maintaining the position of the prosthesis within patient body 84 is illustrated in FIG. 7. In this embodiment, the actuation mechanism for withdrawing sheath 32 relative to shaft 34 is contained in a removable actuation housing 86. Housing 86 is coupled to introducer valve 82 using a brace rod 88.

Although housing 86 and the actuation mechanism therein may be reused for several deployment procedures, the cost of such a system is generally higher than the delivery system illustrated in FIG. 2, particularly when repeated sterilization of the housing and actuation mechanism are considered. Additionally, the use of an actuation handle which rotates perpendicularly to the axis of sheath 32 may lead to inadvertent axial movement of the prosthesis during deployment. This can be particularly problematic when runners 42 are exposed about the perimeter of the body lumen, as any distal advancement of the runners may lead to injury or penetration through the luminal wall.

Figure 8:
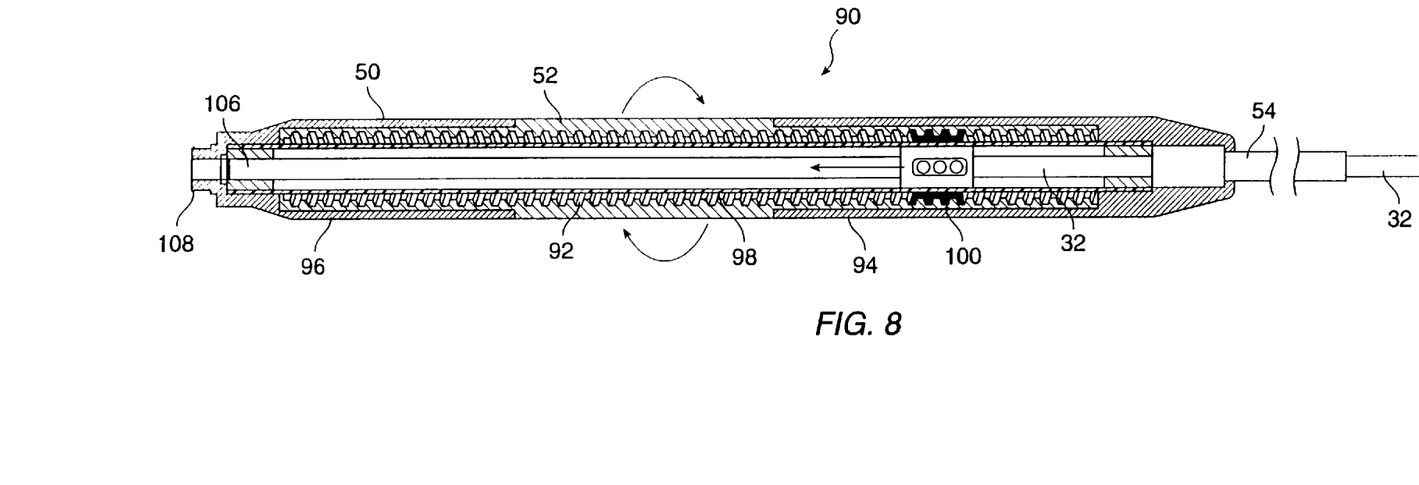
FIG. 8 is a cross-sectional view showing the actuation mechanism of the deployment system of FIG. 2.
Figure 9:
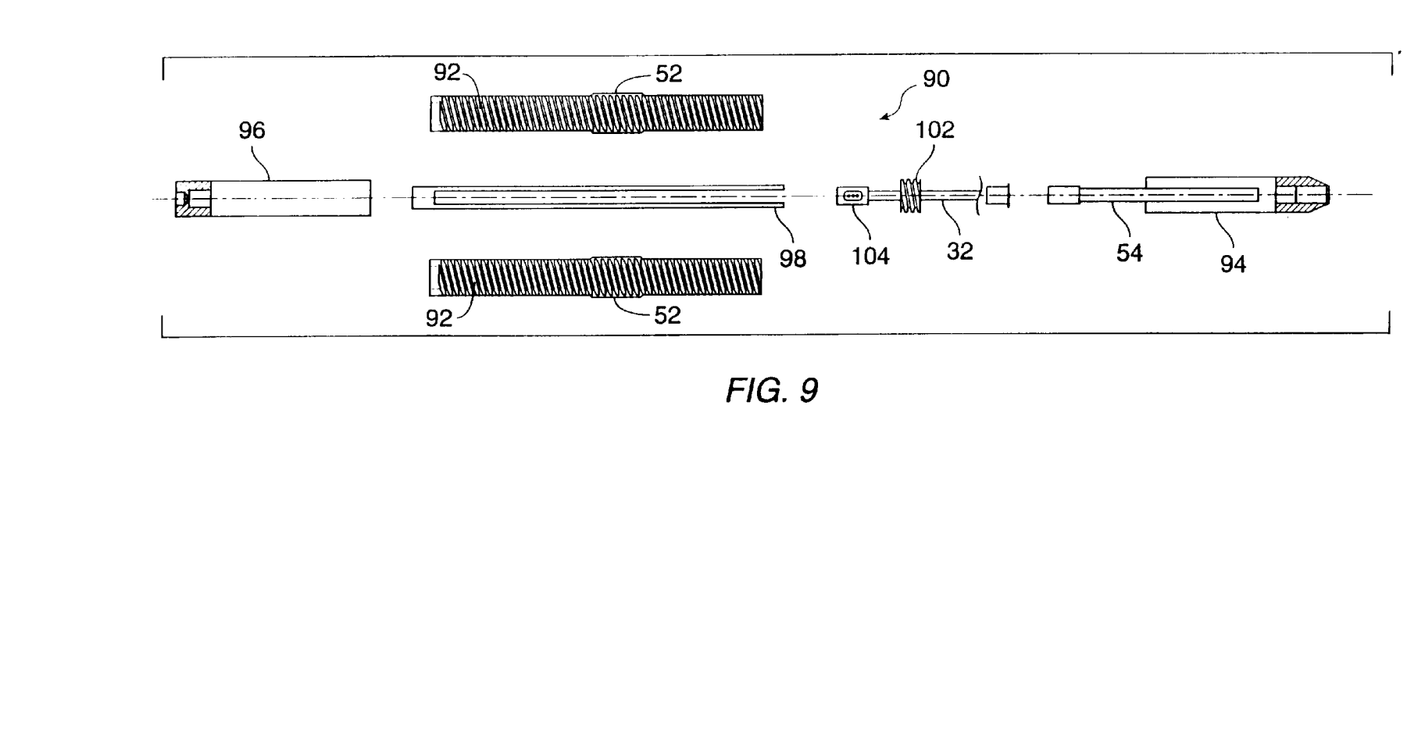
FIG. 9 is an exploded view showing the components of the actuation mechanism of FIG. 8.

An actuation mechanism 90 which converts the axial rotation of handle 52 to axial translation of sheath 32 can be understood with reference to FIGS. 8 and 9. Handle 52 comprises a tubular structure having internal threads 92. Housing 50 includes a distal housing portion 94 and a proximal housing portion 96. These housing portions are held together by a slotted tube 98 extending axially within the threaded handle.

A slider 100 is affixed to the proximal end of sheath 32. Slider 100 includes a threaded ring 102 encircling slotted tube 98, and an inner body 104 which rides within the slotted tube. Threaded ring 102 is affixed to inner body 104 by set screws, tabs protruding radially from the inner body, tabs protruding radially inwardly from the thread ring, or the like. Regardless, some structure of slider 100 extends radially through the slots of slotted tube 98, so that the slotted tube rotationally restrains slider 100.

A reinforcing rod 106 extends distally from proximal portion 96 of housing 50. Reinforcing tube 106 extends through slider 100 to near the distal end of housing 50, and is slidingly received in the lumen of sheath 32. Connector 56 is couplable to a proximal fitting 108. Connector 56 is affixed to shaft 34, so that housing 50 maintains axial alignment between outer tube 54 and shaft 34 when the connector 56 is attached to proximal fitting 108. Reinforcing tube 106 prevents buckling of shaft 34 as slider 100 moves proximally.

Sheath 32 is withdrawn proximally by rotating handle 52 relative to housing 50. As threaded ring 102 of slider 100 engages internal threads 92 of handle 52, and as slotted tube 98 rotationally restrains slider 100 within housing 50, rotation of the handle pulls the slider and attached graft cover axially as shown. In this embodiment, internal threads 92 are constant along the length of handle 52, so that a particular displacement of the handle relative to the housing will effect a consistent axial displacement of the slider regardless of the slider's position. Such constant internal threads will generally have a pitch of between about 0.125 and 0.250, providing a total mechanical advantage in a range from about 4:1 to 3:1 between handle 52 and sheath 32. As will be described hereinbelow, the threads will often have two or more leads, so that the distance between adjacent threads may be ½ (or less) the thread pitch.

Figure 10:
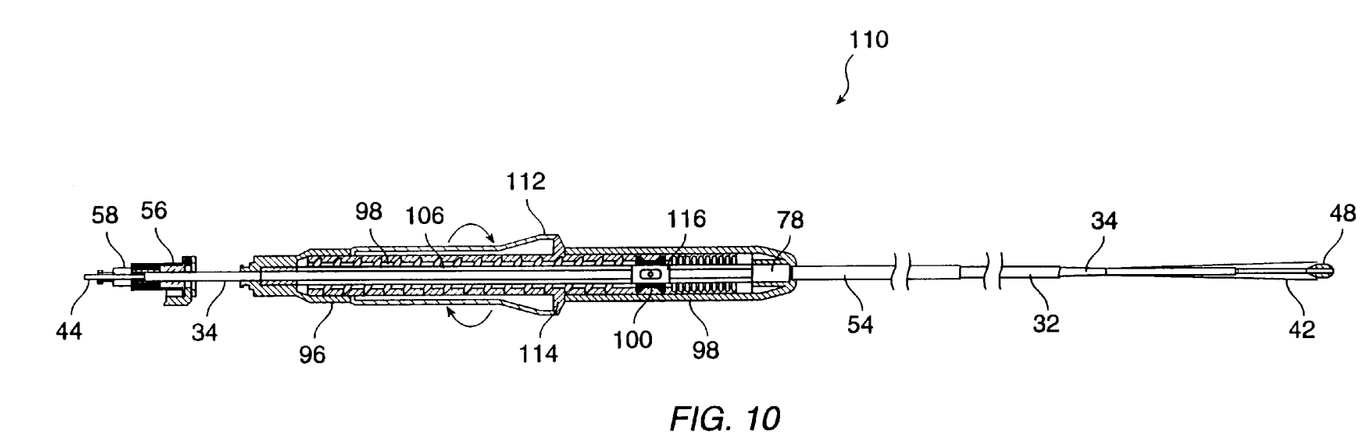
FIGS. 10 and 11 are a cross-sectional view and a side view, respectively, of an alternative deployment system having an actuation mechanism including threads which vary in pitch.
Figure 11:
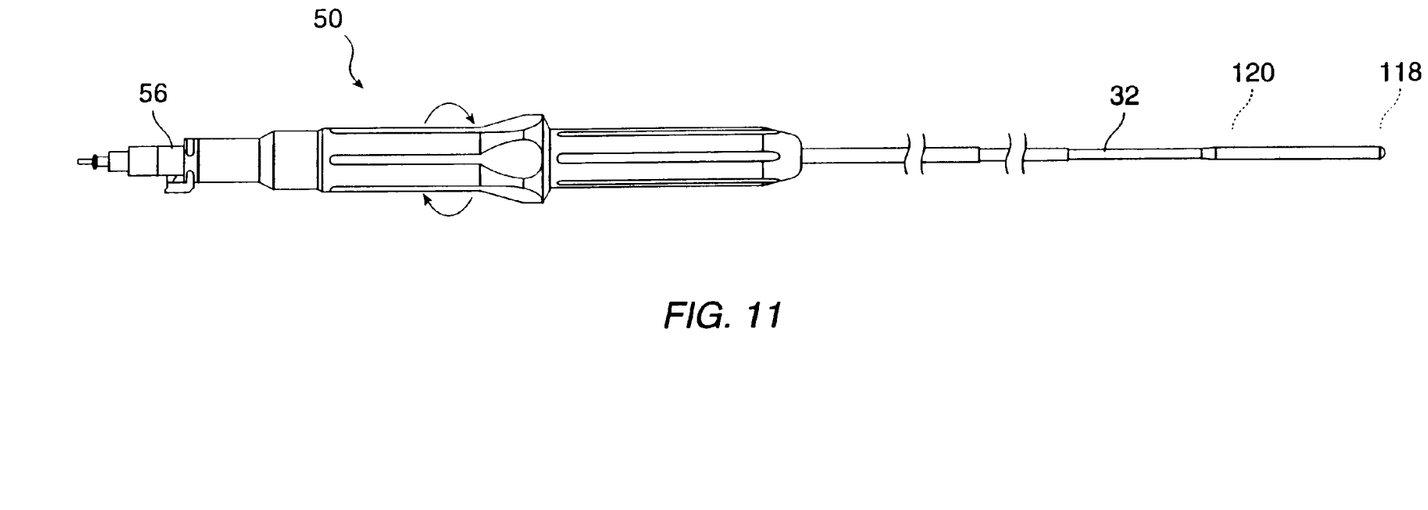

A variable displacement delivery system 110 is illustrated in FIGS. 10 and 11. Variable pitch delivery system 110 includes many of the same components described above, but makes use of a handle 112 having variable pitch internal threads 114. Variable threads 114 have a relatively small pitch adjacent the distal end of handle 112 so that each rotation of the handle moves sheath 32 proximally a relatively small axial distance during the initial phases of deployment. This provides an increased mechanical advantage between the handle and the sheath, helping the physician to overcome the large static frictional forces between the prosthesis and the surrounding sheath. This enhanced mechanical advantage also helps overcome any invagination of the prosthetic frame into the surrounding sheath material. As a result, the distal end of the prosthesis (which is deployed first) will be very gradually released, allowing the physician to verify the accuracy of the deployment position as the prosthesis initially engages the surrounding body lumen. These distal threads will generally have a pitch of between about 0.125 and 0.375, providing a mechanical advantage in the range from about 4:1 to about 2.5:1.

While it is possible to use a constant thread delivery system having a relatively small pitch, this requires repeated rotation of the handle for a considerable amount of time. Additionally, frictional forces between the prosthesis and surrounding sheath decrease once the static frictional forces have been overcome and the sheath begins to move, as dynamic frictional forces are typically lower than static frictional forces. Additionally, as more and more of the prosthesis is released from the surrounding sheath, the total normal force between the prosthesis and the sheath decreases. This acts to further reduce the friction of deployment. The expanded portion of the prosthesis may even help pull the remaining compressed portion axially as the prosthesis expands within the surrounding runners. Finally, once an end of the prosthesis has firmly engaged the surrounding body lumen, the relationship between the prosthesis and the surrounding body lumen is largely set, so that deployment can proceed safely at a more rapid rate. As a result of all these interactions, it is generally desirable to decrease the mechanical advantage between handle 112 and sheath 32 as the sheath moves from a distal position 118 over the prosthesis to a proximal position 120, at which the prosthesis is fully deployed.

Figure 12:
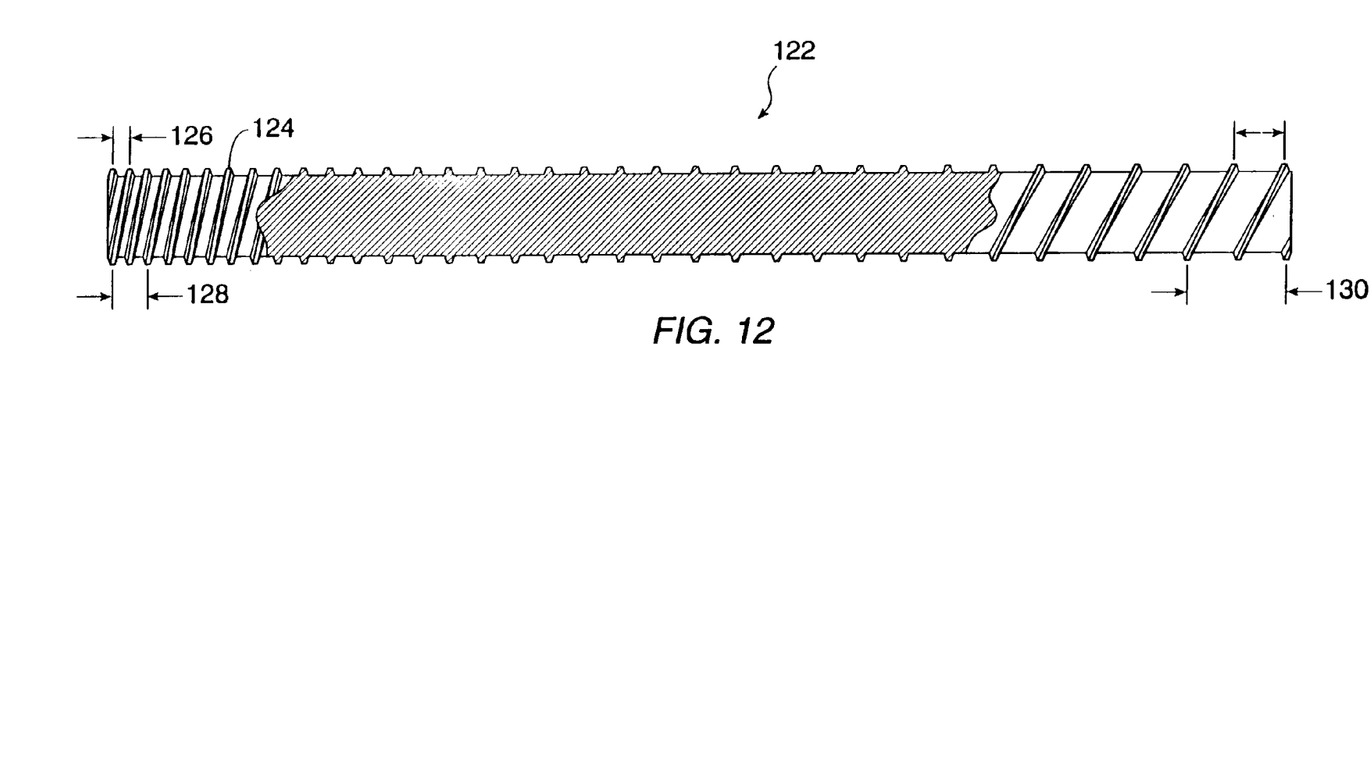
FIG. 12 illustrates a mandrel for forming variable pitch threads for use in the deployment system of FIG. 10.

The use of variable threads 114 and the interaction between handle 112, slider 100, and the slotted tube 98 can be understand with reference to FIGS. 12–17. FIG. 12 illustrates a mandril 122 over which handle 114 is molded to impose variable threads 114. The handle will often be molded in two halves over mandrel 122, with the two halves bonded axially. Mandrel 122 includes external threads 124 which vary in pitch along the axial length of the mandrel. Preferably, threads 124 comprise multi-lead threads having two or more helical thread elements. As a result, a distance 126 between adjacent thread elements is only one half of the pitch 128 at the distal end of mandrel 122. The use of multi-lead threads allows multiple elements to extend axially from the slider to engage the surrounding threads, and thereby enhances the stability of the slider.

As described above, distal pitch 128 is significantly less than a proximal pitch 130, so that rotation of the handle at a constant speed results in increased axial speed of the sheath relative to the prosthesis. Each rotation of handle 112 preferably moves sheath 32 an axial distance of about 0.25 inches when sheath 32 is adjacent covered position 118, while this same rotation of the handle preferably moves the sheath an axial distance of about 0.75 inches when the sheath is adjacent the deployed position 120. In other words, in the exemplary embodiment distal pitch 128 is about 0.25 inches, while proximal pitch 130 is about 0.75 inches. The threads may vary linearly between the proximal and distal ends (as illustrated in FIG. 12), or may vary substantially stepwise as illustrated in FIG. 10. Still further alternatives are possible, such as a quadratic variation in pitch along the axial length of the threads.

Figure 13:
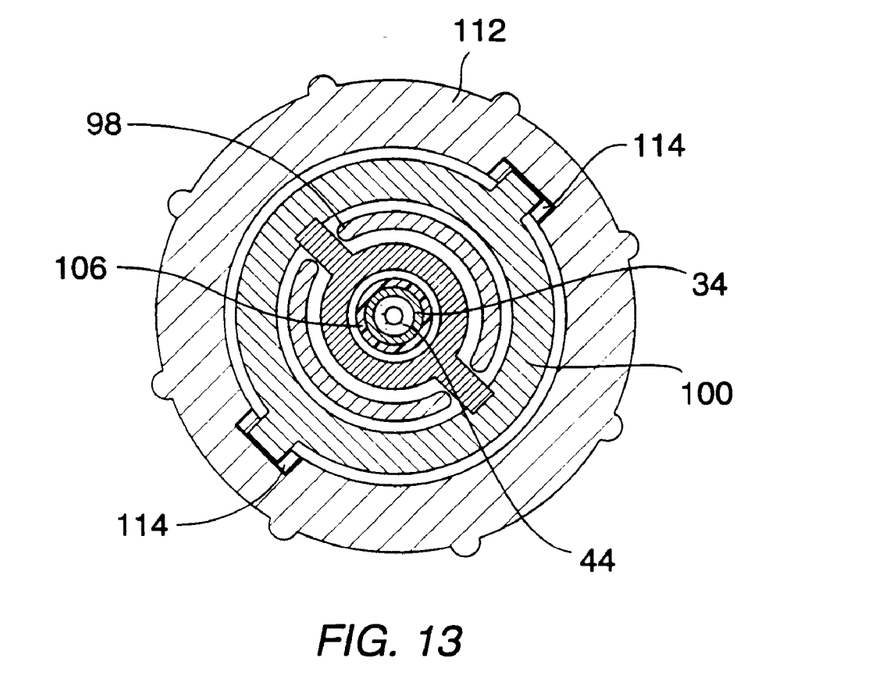
FIG. 13 is a cross-sectional view through the actuation handle of the deployment system of FIG. 10.
Figure 14:
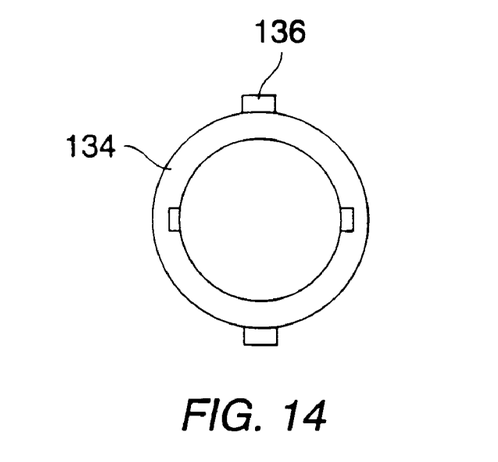
FIGS. 14 through 17 illustrate components of the actuation system for use in the deployment systems of FIGS. 2 and 10.
Figure 15:
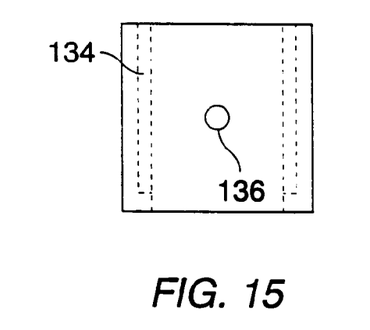
Figure 16:
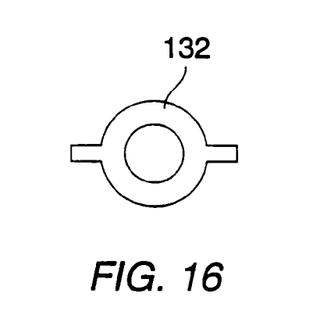
Figure 17:
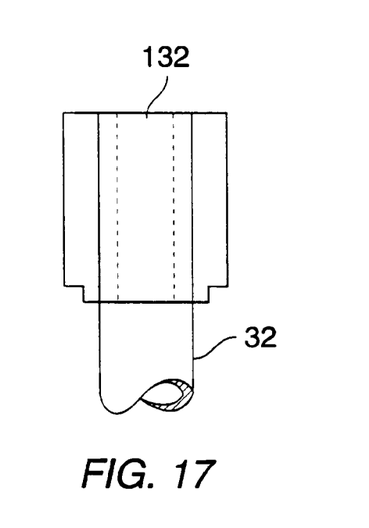

As can be seen in FIGS. 13 through 15, slider 100 may be formed by bonding a finned inner body 132 to an outer ring 134. Outer ring 134 includes opposed pins 136 which extend into the two helical elements of internal variable threads 114 in handle 112. The use of pins rather than external threads on outer ring 134 prevents binding between slider 100 and the handle when the pitch of the threads changes. Also illustrated in FIG. 13 is the interaction of slotted tube 98 and slider 100, whereby the slotted tube rotationally restrains the slider when handle 112 rotates. In some embodiments, slider 100 may include only an inner or outer body. For example, an inner body may have pins which extend through the slotted tube and into variable threads 114, or an outer body may have fins extending into the slotted tube. The use of inner and outer bodies may enhance the stability of the slider to prevent binding.

Generally, delivery system 30 (including housing 50 and actuation mechanism 90) will be formed from inexpensive polymeric materials, and will be undetachably secured together so that the delivery system is disposable after use. In the exemplary embodiment, core shaft 44 comprises a polyester ethylketone (PEEK), while shaft 34 may comprise a high-strength polymer such as PEBAXT™. Slider 100 will typically be formed from molded polymers such as polycarbonate, while reinforcing tube 106 and slotted tube 98 may be formed from stainless steel or thermoplastic. Handle 112 and housing 50 will also typically comprise molded polymer structures.

Connector 56 (and the associated fitting at the proximal end of housing 50) is commercially available from Colder Products Company of St. Paul, Minn., under model number MPC 170-04T. Those skilled in the art should recognize that delivery system 30 will typically be substantially sealed to maintain hemostasis, typically using o-rings to seal between reinforcing tube 106 and sheath 32, as well as between reinforcing rod 106 and shaft 34. The reinforcing rod will typically extend substantially through housing 50, but will not extend distally significantly beyond the housing to allow the delivery system to flex within the body lumen. As illustrated in FIG. 11, such flexibility may be enhanced by decreasing the diameter of sheath 32 proximally of the prosthesis.

While the exemplary embodiment of the present invention has been described in substantial detail by way of example and for clarity of understanding, a number of adaptations, modifications, and changes will be obvious to those skilled in the art. Hence, the scope of the present invention is limited solely by the appended claims.

What is claimed is:

1. A delivery system for use with a tubular endoluminal prosthesis, the delivery system comprising:

a sheath having a proximal end, a distal end, and a lumen capable of receiving the prosthesis near the distal end;

a member in the lumen of the sheath, the member adapted for expelling the prosthesis from the lumen as the sheath moves from a first position to a second position relative to the member; and an actuation mechanism attached to the member and coupling a handle to the sheath with a mechanical advantage which varies as the sheath moves between the first position and the second position such that a displacement of the handle relative to the member effects a first displacement of the sheath relative to the member when the sheath is adjacent the first position, and such that the handle displacement effects a second displacement of the sheath when the sheath is adjacent the second position, the first sheath displacement being smaller than the second sheath displacement.

2. A delivery system as claimed in claim 1, wherein the mechanical advantage when the sheath is adjacent the first position is adapted to overcome static frictional forces between the prosthesis and the sheath, and wherein the mechanical advantage when the sheath is adjacent the second position is adapted to overcome dynamic frictional forces which are smaller than the static frictional forces, and to enhance the speed of expelling the prosthesis from the sheath.

3. A delivery system for use with a tubular endoluminal prosthesis, the delivery system comprising:

a sheath having a proximal end, a distal end, and a lumen capable of receiving the prosthesis near the distal end;

a member in the lumen of the sheath, the member adapted for expelling the prosthesis from the lumen as the sheath moves from a first position to a second position relative to the member; and an actuation mechanism attached to the member and coupling a handle to the sheath with a mechanical advantage which varies as the sheath moves between the first position and the second position, wherein the actuation mechanism comprises threads defining an axis, and wherein a pitch of the threads varies along said axis of the threads.

4. A delivery system as claimed in claim 3, wherein the threads comprise multiple-lead threads, and wherein the actuation mechanism further comprises a slider having pins which engage the threads so rotation of one member of the group consisting of the slider and the threads effects axial movement of the sheath relative to the member.

5. A delivery system as claimed in claim 3, wherein the handle comprises a tubular structure substantially aligned with the sheath, the handle coupled to the threads so that rotation of the handle about the axis of the sheath effects relative movement between the sheath and the member.

6. A delivery system as claimed in claim 1, wherein the actuation mechanism, the sheath, and the member comprise undetachably coupled diposable polymer structures.

7. A prosthetic delivery system for use with a radially expandable tubular endoluminal prosthesis, the delivery system comprising:

a sheath having a proximal end, a distal end, an axis therebetween, and a lumen capable of receiving the prosthesis near the distal end;

a member in the lumen for expelling the prosthesis from the lumen as the sheath moves from a first position to a second position relative to the member; and an actuation mechanism attached to the member, the actuation mechanism coupling the sheath to a handle, the handle comprising a tubular structure disposed substantially coaxially with the sheath, the actuation mechanism comprising a slider and threads coupling the tubular structure to the slider, wherein the slider and threads are disposed within the tubular structure, the tubular structure rotatable about an axis substantially parallel to the axis of the sheath to effect axial movement of the slider thereby causing the sheath to move from the first position to the second position.

8. A delivery system as claimed in claim 7, wherein the actuation mechanism, the sheath, and the member comprise undetachably coupled disposable polymer structures.

9. A delivery system as claimed in claim 7, wherein, the slider is rotationally restrained relative to a housing so that the slider moves axially when the handle rotates.

10. A prosthetic delivery system for use with a radially expandable tubular endoluminal prosthesis, the delivery system comprising:

a sheath having a proximal end, a distal end, an axis therebetween, and a lumen capable of receiving the prosthesis near the distal end;

a member in the lumen for expelling the prosthesis from the lumen as the sheath moves from a first position to a second position relative to the member; and an actuation mechanism attached to the member coupling the sheath to a handle, the handle rotatable about an axis substantially parallel to the axis of the sheath;

wherein the rotatable handle has an inner surface which defines threads and a slider disposed therein, the slider being coupled to the sheath and engaging the threads to draw the sheath proximally when the threads rotate.

11. A delivery system as claimed in claim 10, wherein a pitch of the threads varies along an axial length of the rotatable handle portion.

12. A delivery system as claimed in claim 10, wherein the actuation mechanism can move the sheath axially a distance of between about 7.0 inches and 10.0 inches relative to the member.

13. A method for deploying a radially expandable tubular endoluminal prosthesis, the method comprising:

positioning the prosthesis at a target location in a body lumen while the prosthesis is disposed within a lumen of a sheath;

releasing the prosthesis from the sheath by actuating a handle to withdraw the sheath proximally from a first position to a second position, a displacement of the handle effecting a first displacement of the sheath when the sheath is adjacent the first position, the handle displacement effecting a second displacement of the sheath which is larger than the first sheath displacement when the sheath is adjacent the second position.

14. A method for deploying a radially expandable tubular endoluminal prosthesis, the method comprising:

positioning the prosthesis at a target location in a body lumen while the prosthesis is disposed within a lumen of a sheath;

rotating a handle about an axis which is parallel to an axis of the sheath to move the sheath axially from over the prosthesis thereby releasing the prosthesis from the sheath, the handle having an inner surface defining threads and a slider disposed therein, the slider engaging the threads and rotationally restrained by a restraint structure disposed within the handle so that the slider draws the sheath proximally when the handle rotates.

15. A method for deploying a radially expandable tubular endoluminal prosthesis, the method comprising:

inserting the prosthesis into the body lumen through an introducer valve while the prosthesis is disposed within a lumen of a sheath;

inserting an outer tube through the introducer valve;

positioning the prosthesis at a target location in the body lumen;

releasing the prosthesis from the sheath by withdrawing the sheath and restraining the prosthesis with a member disposed within the sheath; and immovably affixing the member axially relative to the outer tube so that friction between the introducer valve and the outer tube helps prevent movement of the prosthesis from the target location.

16. A prosthetic delivery system for with a radially expandable tubular endoluminal prosthesis, the delivery system comprising:

a sheath having a proximal end, a distal end, an axis therebetween, and a lumen capable of receiving the prosthesis near the distal end;

a member in the lumen for expelling the prosthesis from the lumen as the sheath moves from a first position to a second position relative to the member; and an actuation mechanism attached to the member, the actuation mechanism coupling the sheath to a handle, the handle rotatable about an axis substantially parallel to the axis of the sheath to effect movement of the sheath from the first position to the second position;

wherein the actuation mechanism further comprises a slider and threads coupling the handle portion to the slider, the slider being rotationally restrained relative to a housing so that the slider moves axially when the handle rotates;

wherein a pitch of the threads varies along an axial length of the rotatable handle portion.

17. A prosthetic delivery system for use with a radially expandable tubular endoluminal prosthesis, the delivery system comprising:

a sheath having a proximal end, a distal end, an axis therebetween, and a lumen capable of receiving the prosthesis near the distal end;

a member in the lumen for expelling the prosthesis from the lumen as the sheath moves from a first position to a second position relative to the member; and an actuation mechanism attached to the member, the actuation mechanism coupling the sheath to a handle, the handle rotatable about an axis substantially parallel to the axis of the sheath to effect movement of the sheath from the first position to the second position;

wherein the actuation mechanism can move the sheath axially a distance of between about 7.0 inches and 10.0 in relative to the member.

18. A prosthetic delivery system for use with a radially expandable tubular endoluminal prosthesis, the delivery system comprising:

a sheath having a proximal end, a distal end, an axis therebetween, and a lumen capable of receiving the prosthesis near the distal end;

a member in the lumen for expelling the prosthesis from the lumen as the sheath moves from a first position to a second position relative to the member; and an actuation mechanism attached to the member, the actuation mechanism coupling the sheath to a handle, an inner surface of the handle defining threads, wherein a pitch of the threads varies along an axis of the threads, the handle rotatable about an axis substantially parallel to the axis of the sheath to effect movement of the sheath from the first position to the second position.

19. A delivery system as claimed in claim 7, wherein a pitch of the threads varies along an axial length of the rotatable handle portion.

20. A delivery system as claimed in claim 7, wherein the actuation mechanism can move the sheath axially a distance of between about 7.0 inches and 10.0 inches relative to the member.

21. A delivery system as claimed in claim 10, wherein the slider is rotationally restrained relative to a housing so that the slider moves axially when the handle rotates.

22. A delivery system as claimed in claim 19, further comprising an outer tube disposed over the sheath and coupled to the housing so that the outer tube remains axially aligned with the member when the sheath moves from the first position to the second position.

23. A delivery system as claimed in claim 20, further comprising an introducer valve capable of maintaining hemostasis around the sheath and around the outer tube, and sliding seals between the member and the sheath and between the outer tube and the sheath.

24. A delivery system for use with a radially expandable tubular endoluminal prosthesis, the delivery system comprising:

a sheath having a proximal end, a distal end, an axis therebetween, and a lumen capable of receiving the prosthesis near the distal end;

a member in the lumen for expelling the prosthesis from the lumen as the sheath moves from a first position to a second position relative to the member;

a tubular handle disposed adjacent the proximal end of the sheath;

a slider mechanically coupled within the tubular handle by threads; and a restraint structure disposed within the tubular handle and rotationally restraining the slider so that rotation of the handle moves the sheath toward the second position, and so that an outer surface of the handle is radially unobstructed.

* * * * *